(12) United States Patent
Derrer et al.

(10) Patent No.: US 7,459,581 B2
(45) Date of Patent: Dec. 2, 2008

(54) ANTI-BACTERIAL COMPOUNDS

(75) Inventors: Samuel Derrer, Fällanden (CH);
Andreas Natsch, Uetikon (CH); Bernd Traupe, Hamburg (DE); Melanie Stang, Möhlin (DE)

(73) Assignee: Givaudan S.A., Vernier (CH)

( * ) Notice: Subject to any disclaimer, the term of this patent is extended or adjusted under 35 U.S.C. 154(b) by 0 days.

(21) Appl. No.: 11/661,833

(22) PCT Filed: Aug. 31, 2005

(86) PCT No.: PCT/CH2005/000509

§ 371 (c)(1),
(2), (4) Date: May 2, 2007

(87) PCT Pub. No.: WO2006/026876

PCT Pub. Date: Mar. 16, 2006

(65) Prior Publication Data

US 2008/0070985 A1    Mar. 20, 2008

(30) Foreign Application Priority Data

Sep. 6, 2004 (GB) .................. 0419694.5

(51) Int. Cl.
*C07C 229/00* (2006.01)
*C07C 69/66* (2006.01)
*A61K 31/22* (2006.01)

(52) U.S. Cl. .................. 560/155; 560/179; 514/546; 514/551

(58) Field of Classification Search .................. 560/155, 560/179; 514/546, 551
See application file for complete search history.

(56) References Cited

U.S. PATENT DOCUMENTS 4,216,227 A    8/1980    Cook et al.
5,015,419 A    5/1991    Moreau et al.

OTHER PUBLICATIONS

Inoue, Y., et al. "Antibacterial Characteristics of Newly Developed Amphiphilic Lips and DNA-Lipid Complexes Against Bacteria", Journal of Biomedical Materials Research (Wiley Periodicals, Inc., 2003), pp. 204-209, XP-002357414.

*Primary Examiner*—Sikarl A Witherspoon
(74) *Attorney, Agent, or Firm*—Curatolo Sidoti Co., LPA; Joseph G. Curatolo; Salvatore A. Sidoti

(57) ABSTRACT

Ester compounds of the formula I-a

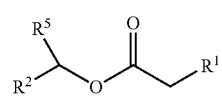

wherein $R^1$ is selected from OH, $NH_2$ and $NH_3^+X^-$, wherein X is an inorganic anion, wherein $R^2$ is a singly-branched saturated or unsaturated aliphatic hydrocarbon moiety selected from $C_7$-$C_{15}$, wherein $R^5$ is selected from H, and a linear saturated or unsaturated aliphatic hydrocarbon moiety selected from $C_6$-$C_{14}$, and wherein $R^2$ and $R^5$ together have a total of 7 to 15 carbon atoms; that are useful as antibacterial or antifungal compounds in consumer products.

44 Claims, No Drawings

ANTI-BACTERIAL COMPOUNDS

CROSS REFERENCE TO RELATED APPLICATIONS

This application is a national stage application of International Application No. PCT/CH2005/000509, filed 31 Aug. 2005, which claims the benefit of Application No. GB 0419694.5, filed 6 Sep. 2004 from which applications priority is claimed.

The present invention relates to antibacterial or anti-fungal compounds, their use in consumer products and methods of making same.

As used herein, the term "anti-bacterial" or "anti-fungal" used in connection with a compound of the present invention is intended to refer to a compound that displays bacteriostatic or bactericidal, or fungicidal or fungistatic properties, or both, depending on the condition to be prevented or treated and the concentration of compound or compounds employed.

Bacterial or fungal conditions are caused by microorganisms such as bacteria or fungi and may range from body malodour such as axillary malodour and foot odour to manifestations of the skin or scalp such as acne, Athlete's foot or dandruff. Body malodour is formed when certain compounds contained in fresh perspiration, which are essentially odourless, are catabolised by bacteria such as *Staphylococci* and *Corynebacteria* both of which genera belong to the class of gram-positive Eubacteriaceae. Regarding foot malodour, a major cause of this condition is the presence of *Brevibacteria* under high humidity and low aeration conditions. Acne is another skin manifestation attributed to a bacterial origin. The microorganism thought to be responsible is *Propionibacterium acnes*.

Dandruff is a condition of the scalp characterized by excessive scaling and is believed to be caused by the scalp-inhabiting yeasts of the genus *Malassezia furfur* and *Malassezia ovalis*. Athlete's foot or *Tinea pedis* is a condition of the feet occurring especially under conditions of enhanced humidity when fungi of the genera *Trichophyton* and *Epidermophytum floccosum* colonise the skin between the toes, which results in maceration and peeling of the skin and an itching sensation.

Anti-bacterial or anti-fungal agents are used in consumer products to prevent or treat a variety of conditions mentioned above.

A principal method by which anti-bacterial or anti-fungal compositions prevent or treat the aforementioned conditions employs active agents that reduce such bacterial or fungal flora on the skin or in the household. However, a problem with many known anti-bacterial agents or anti-fungal agents is that they may affect the entire microbial flora and not just the targeted micro-organism.

Many anti-bacterial or anti-fungal agents are useful in treating one or more of the aforementioned conditions. Triclosan is an anti-bacterial agent used in many products, including household and personal care products. However, being a chlorinated product, its use is questioned by consumer protection organisations. Further, it has especially high activity against low odour-forming *Staphylococci* bacteria, and as such may create favourable conditions in which the more problematic *Corynebacteria* may thrive.

There have been many disclosures in the art of perfume ingredients that have anti-bacterial or anti-fungal properties. One such natural fragrance compound is Farnesol. However, the problem with using perfume ingredients as anti-bacterial agents is that, to obtain anti-bacterial effects, they must generally be employed at higher levels than one would customarily wish to use in fragrance applications. Further, even if such materials could be used to achieve an anti-bacterial effect at low levels suitable for perfumers, their volatility is often so high that they will only be effective for a short period of time before they evaporate and leave the skin.

Non-perfume compounds have been employed as antibacterial and anti-fungal agents in household and consumer products including personal care products and products to be applied to the skin. The use of monolaurin-glycerol and other glycerol esters or glycerol mono-ethers have been described in the art.

Applicant has now found a new class of ester compounds that are odourless and that have a reasonable residence time on the skin of a user, thereby to exert a desirable anti-bacterial effect against bacteria.

Therefore the invention provides in one of its aspects a compound according to the formula I-a

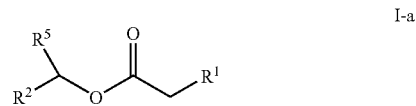

wherein $R^1$ is selected from OH, $NH_2$ and $NH_3^+X^-$, wherein X is an inorganic anion, for example $Cl^-$, wherein $R^2$ is a singly-branched saturated or unsaturated aliphatic hydrocarbon moiety selected from $C_7$-$C_{15}$, wherein $R^5$ is selected from H, and a linear saturated or unsaturated aliphatic hydrocarbon moiety selected from $C_6$-$C_{14}$, and wherein $R^2$ and $R^5$ together have a total of 7 to 15 carbon atoms, and with the proviso that the ester compound is not selected from 2-ethylhexyl glycinate and ethylhexyl glycolate.

2-ethylhexyl glycinate is described in Mongkol et al., Macromolecules 1999, 7361-7369 as a starting material to prepare polydiacetylene polymers. Ethylhexyl glycolate is described in U.S. Pat. No. 5,015,419 as an intermediate to produce antimicrobial yarn lubricants.

In another of its aspects the invention provides a compound according to the formula I-b

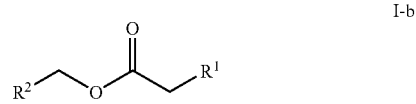

wherein $R^1$ is selected from OH, $NH_2$ and $NH_3^+X^-$, wherein X is an inorganic anion, for example $Cl^-$, and wherein $R^2$ is a singly-branched saturated or unsaturated aliphatic hydrocarbon moiety selected from $C_7$-$C_{15}$, and with the proviso that the ester compound is not selected from 2-ethylhexyl glycinate and ethylhexyl glyconate.

By "singly-branched" is meant a hydrocarbon moiety with a main carbon and one carbon chain branch.

$C_7$-$C_{15}$ specifically include $C_7$, $C_8$, $C_9$, $C_{10}$, $C_{11}$, $C_{12}$, $C_{13}$, $C_{14}$ and $C_{15}$.

Preferred compounds are compounds according to formula I wherein $R^2$ is selected from a saturated hydrocarbon moiety; and a hydrocarbon moiety according to formula II,

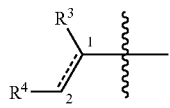

II wherein the bond between C1 and C2 (C1 and C2 being the carbon atoms in position 1 or 2 as indicated in formula II) is a single bond, or preferably a double bond, and $R^3$ and $R^4$ are independently selected from methyl, ethyl, propyl, butyl, pentyl, hexyl, heptyl, octyl, nonyl, decyl, undecyl and dodecyl.

For $R^3$ and $R^4$, this allows for the following combinations as indicated in table 1 and 2. Each double column indicates $R^2$ in the first row, and the different possibilities of $R^3$ and $R^4$ in the following rows of each double column.

personal care product, as a part of a shampoo composition for application to the scalp in the treatment of dandruff, or as part of a composition for application to the feet of a patient in need of treatment, to treat fungal conditions of the feet, such as Athlete's Foot.

Compounds of the present invention exert a bacteriostatic effect that is comparable to or better than that of known bacteriostatic agents, for example Triclosan, glycerol esters, such as monolaurin-glycerol, known glycerol ethers, or known fragrance oils. In tests, the bacteriostatic Minimal Inhibitory Concentration (MIC) of the compounds ranges from 0.0005% to greater than 0.25% (weight/volume) depending on the micro-organism treated. These values, including the values for many of the common bacteria, and in particular the *Corynebacteria*, compare favourably with those of known glycerol mono-esters or mono-ethers, Triclosan, and a known antibacterial fragrance compound, Far-

TABLE 1

| $R^2 = C_7$ | | $R^2 = C_8$ | | $R^2 = C_9$ | | $R^2 = C_{10}$ | | $R^2 = C_{11}$ | |
|---|---|---|---|---|---|---|---|---|---|
| $R^3$ | $R^4$ | $R^3$ | $R^4$ | $R^3$ | $R^4$ | $R^3$ | $R^4$ | $R^3$ | $R^4$ |
| methyl | butyl | methyl | pentyl | methyl | hexyl | methyl | heptyl | methyl | octyl |
| ethyl | propyl | ethyl | butyl | ethyl | pentyl | ethyl | hexyl | ethyl | heptyl |
| propyl | ethyl | propyl | propyl | propyl | butyl | propyl | pentyl | propyl | hexyl |
| butyl | methyl | butyl | ethyl | butyl | propyl | butyl | butyl | butyl | pentyl |
| | | pentyl | methyl | pentyl | ethyl | pentyl | propyl | pentyl | butyl |
| | | | | hexyl | methyl | hexyl | ethyl | hexyl | propyl |
| | | | | | | heptyl | methyl | heptyl | ethyl |
| | | | | | | | | octyl | methyl |

TABLE 2

| $R^2 = C_{12}$ | | $R^2 = C_{13}$ | | $R^2 = C_{14}$ | | $R^2 = C_{15}$ | |
|---|---|---|---|---|---|---|---|
| $R^3$ | $R^4$ | $R^3$ | $R^4$ | $R^3$ | $R^4$ | $R^3$ | $R^4$ |
| methyl | nonyl | methyl | decyl | methyl | undecyl | methyl | dodecyl |
| ethyl | octyl | ethyl | nonyl | ethyl | decyl | ethyl | undecyl |
| propyl | heptyl | propyl | octyl | propyl | nonyl | propyl | decyl |
| butyl | hexyl | butyl | heptyl | butyl | octyl | butyl | nonyl |
| pentyl | pentyl | pentyl | hexyl | pentyl | heptyl | pentyl | octyl |
| hexyl | butyl | hexyl | pentyl | hexyl | hexyl | hexyl | heptyl |
| heptyl | propyl | heptyl | butyl | heptyl | pentyl | heptyl | hexyl |
| octyl | ethyl | octyl | propyl | octyl | butyl | octyl | pentyl |
| nonyl | methyl | nonyl | ethyl | nonyl | propyl | nonyl | butyl |
| | | decyl | methyl | decyl | ethyl | decyl | propyl |
| | | | | undecyl | methyl | undecyl | ethyl |
| | | | | | | dodecyl | methyl |

Even more preferred are compounds according to formula I with $R^2$ a hydrocarbon moiety according to formula II and wherein $R^3$ and $R^4$ are selected from the following combinations: R3=ethyl and R4=propyl, R3=butyl and R4=methyl, R3=butyl and R4=pentyl, R3=hexyl and R4=propyl, R3=hexyl and R4=heptyl, R3=octyl and R4=pentyl.

A preferred anti-bacterial effect is an effect against human skin bacteria, including typical malodour-forming bacteria present in the human axilla (including *Corynebacterium* and *Staphylococcus*), and typical malodour forming bacteria present on the human foot (including *Brevibacteria*).

A compound according to the present invention exerts good anti-microbial, anti-fungal and/or malodour-counteracting activity when used in consumer products, products applied in the household or on the human body, particularly when applied to the skin or scalp, for example as part of nesol. Further details as to how the MIC test data are generated are provided in Example 10 below.

In addition, some compounds of the present invention exert a bactericidal effect. In tests, the anti-bacterial Minimal Bactericidal Concentration (MBC) of the compounds ranges from 0.0005% to greater than 0.25% (weight/volume) depending on the micro-organism treated. Further details as to how the MBC test data are generated are provided in Example 11 below.

Furthermore, some compounds of the present invention exert an fungistatic effect, in addition to their bacteriostatic or bactericidal effect, as shown in example 12.

Compounds of the present invention may be formed starting from an alcohol $R_2$—$CH_2$—$OH$, wherein $R_2$ is as defined above. Such alcohols are either commonly available or they may be formed from easily-accessible starting materials.

Compounds of formula I with $R^1$=OH are most conveniently prepared in one step from glycolic acid and the corresponding alcohol under acid catalysis, for example using $H_2SO_4$ and toluene.

Compounds of formula I with $R^1$=$NH_2$ or $NH_3^+X^-$ are most conveniently prepared using commercially-available tert.-butyloxycarbonyl glycine as a starting material and the ester is then prepared by reaction with a dicyclohexylcarbodiimide (DCC)-mediated coupling reaction in presence of 4-(N,N-dimethylamino)pyridine (DMAP). The amine-protecting group is subsequently removed under acidic conditions. The esters of formula I are distilled, purified by chromatography or isolated without purification.

Further details of the preparative methods are disclosed in the examples herein below.

The present invention provides in another of its aspects the use of at least one compound as hereinabove described as an active agent in compositions such as consumer products for the prevention or treatment of bacterial conditions and/or fungal conditions, and/or for the elimination or suppression of malodour, particularly conditions or malodour resulting from the presence of malodour-forming bacteria on the human skin (for example, axillary malodour, foot malodour, dandruff, Athlete's foot, and acne).

Further, the invention provides a method of making a product that has at least one of an antibacterial, antifungal and malodour-counteracting effect by admixing an effective amount of an antibacterial, antifungal or malodour-counteracting compound according to the present invention into a product, preferably a consumer product.

Consumer products include household products, cosmetic and personal care products, products for use on the human body, products applied to the human skin, and perfumed consumer goods.

Cosmetic and personal care products, in particular deodorant and antiperspirant cosmetic or personal care products, include soaps, sticks, roll-ons, sprays, pump-sprays, aerosols, deodorant soaps, soap bars, powders, solutions, gels, creams, balms and lotions, eau de Cologne, and eau de toilet, deodorant soaps, shampoos, bath salt, salves, lotions, creams, and ointments.

Perfumed consumer goods include sprays, detergents and solid fragranced products such as powders, soaps, detergent powders, tissues, fabrics, room deodorizers, room deodorizing gels, and candles.

The amount of a compound employed in such a composition will depend upon the nature of the product and the condition to be treated. However, in the case of products that are applied to and left on the skin, it is preferred that a compound or mixtures of compounds be present in said compositions in an amount of about 0.1 to about 2.0% by weight, preferably about 0.1 to 1% by weight.

If a compound or a mixture of compounds is to be used in a composition intended to be applied to, and subsequently rinsed off, the skin or scalp, e.g. a shampoo composition for the treatment of dandruff, then it is preferred to use the compound or mixture of compounds in higher amount, e.g. from about 1.0 to 5.0% by weight.

Depending on the nature of the consumer product, compounds of the present invention may also be combined with art-recognised quantities of other excipients commonly employed in these products; useful selections may be found in <<CTFA Cosmetic Ingredient Handbook>>, J. M. Nikitakis (ed.), 1st ed., The Cosmetic, Toiletry and Fragrance Association, Inc., Washington, 1988, which is hereby incorporated by reference.

In general, excipients may, for example, include colorants, fragrances, solvents, surfactants, colorants, opacifiers, buffers, antioxidants, vitamins, emulsifiers, UV absorbers, silicones and the like. All products can also be buffered to the desired pH using commonly-available excipients in a known manner.

Excipients in deodorant cologne may comprise ethanol and fragrance. Fragrance may be present to the extent of 1 to 10% by weight and the ethanol may be present to make up the mass to 100% by weight.

A typical ethanol-free deodorant stick may comprise polyols, such as propylene glycol; derivatives thereof, such as propylene-glycol-3-myristyl ether (for example Witconol® APM); water; a surfactant such as sodium stearate; and a fragrance. The polyol may be present to the extent of 30 to 40%; the derivatives of the polyol likewise may be present to the extent of 30 to 40%; water may be present to the extent of 10 to 20%; the surfactant may be present to the extent of 5 to 10%; and the fragrance may be present in an amount mentioned above.

A typical antiperspirant stick may comprise excipients such as ethylene glycol monostearate (e.g. from 5 to 10%); Shea butter (e.g. from 3 to 5%); Caprylic/Capric Triglyceride such as Neobee® 1053 (PVO International) (e.g. from about 12 to 15%); phytosterols such as Generol® 122 (Henkel) (e.g. from about 3 to 7%); Dimethicone (DC 345) (e.g. from 30 to 40%); aluminium sesquichlorohydrate (for example from about 15 to 20%); and a fragrance, for example from 1 to 10%.

An antiperspirant aerosol may contain as excipients ethanol, typically to the extent of 10 to 15%; zirconium aluminium tetrachlorohydrate, for example from 3 to 5%; Bentone 38, for example from 1 to 2%; fragrance in an amount aforementioned; and a hydrocarbon propellant, such as S-31, for example for up to 100%.

An antiperspirant pump composition may contain as excipients aluminium sesquichlorohydrate, for example from 15 to 25%; water, for example from 50 to 60%; an octylphenol ethoxylate non-ionic surfactant such as Triton X-102 (Union carbide), for example from 1 to 3%; dimethyl Isosorbide (ICI), for example from 15 to 25%; and a fragrance in an amount as aforementioned.

All percentages mentioned above are in wt %.

In all the above compositions, the compound or mixtures thereof may be used as the sole active agent, or it may be used in conjunction with other active agents such as Triclosan (CAS 3380-34-5) or other commercially available anti-bacterial or anti-fungal agents, or with known fragrance oils having anti-bacterial or anti-fungal properties.

There now follows a series of non-limiting examples that serve to illustrate the invention.

EXAMPLE 1

Overview Synthesis of Compounds According to Formula I

Compounds of formula I are most conveniently prepared by the transformations shown in Scheme 1. Compounds of formula I with $R^1$=OH are accessible in one step from glycolic acid and the corresponding alcohol under acid catalysis (Scheme 1a). In the case of compounds of formula I with $R^1$=$NH_3^+X^-$, commercial tert.-butyloxycarbonyl glycine is used as starting material and the ester effected with a dicyclohexylcarbodiimide (DCC)-mediated coupling reaction (Scheme 1b). The amine protecting group is subsequently removed under acidic conditions. The esters of formula I are distilled, purified by chromatography or isolated without purification.

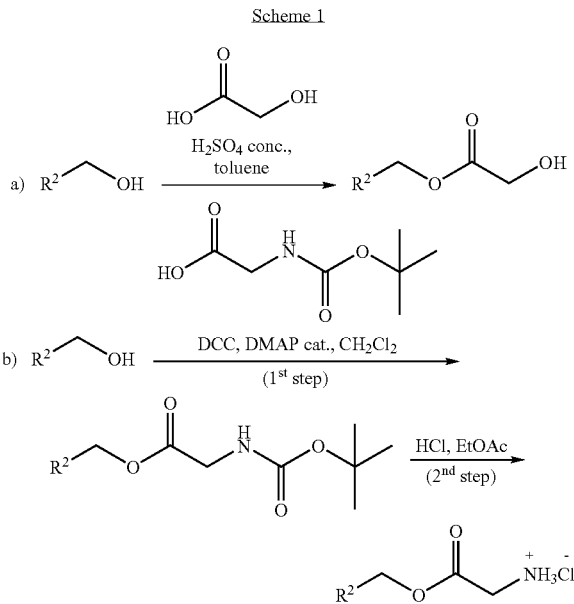

Scheme 1

EXAMPLE 2

General Procedure (A) for the Synthesis of Glycolic Acid Esters According to Formula I with $R^1$=OH A stirred mixture of the alcohol (0.2 mol), glycolic acid (0.2 mol) and sulphuric acid (0.02 mol) in toluene (260 ml) is heated to reflux under Dean-Stark conditions until approximately 0.2 mol water is collected. The mixture is allowed to cool to room temperature and poured into water. This mixture is extracted with tert.-butyl methyl ether and the organic layers are washed with aqueous saturated sodium hydrogencarbonate, water and brine. The combined organic phases are dried over sodium sulfate and concentrated in vacuo to afford the desired glycolate ester compound of formula I as a colourless oil in a yield of about 55-70%.

EXAMPLE 3

General Procedure (B) for the Synthesis of Glycine Esters according to formula I with $R^1$=$NH_3^+Cl^-$ $1^{st}$ step: To a stirred mixture of the alcohol (0.05 mol), tert.-butyloxycarbonyl-glycine (0.055 mol) and N,N-dimethylaminopyridine (0.04 mol) in toluene (180 ml) is added dropwise N,N'-dicyclohexylcarbodiimide (0.06 mol) dissolved in toluene (50 ml) within 20 minutes at room temperature. Stirring is continued for up to 72 h at room temperature or reflux, depending on the nature of the starting alcohol. The resulting white suspension is concentrated and the residue diluted with tert.-butyl methyl ether. The white precipitate is filtered off and washed with tert.-butyl methyl ether. Then the filtrate is washed with aqueous hydrochloric acid (5%) and brine. The organic phase is dried over sodium sulfate and concentrated in vacuo to give the protected glycine ester.

$2^{st}$ step: To hydrochloric acid in ethyl acetate (0.25 mol, 3 M) was added the above crude ester (0.05 mol) at room temperature. The mixture was stirred for 2 h and then concentrated in vacuo. The desired glycine ester compound of formula I is obtained in an overall yield of 65-75% as a white solid or colourless resin.

EXAMPLES 4-6

The compounds of formula I with $R^1$=OH shown below, together with their spectroscopic data, are prepared as described in procedure A with the starting materials chosen as will be apparent to the skilled person.

EXAMPLE 4

Hydroxy-acetic acid 2-ethyl-hexyl ester

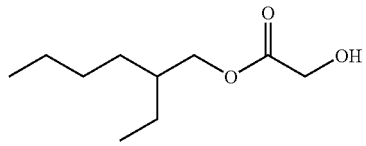

Hydroxy-acetic acid 2-ethyl-hexyl ester

H-NMR (400 MHz, CDCl$_3$, coupling constants in Hz): 0.86-0.93 (6H, m, 2×CH$_3$); 1.23-1.41 (8H, m, 4×CH$_2$); 1.55-1.65 (1H, m, CH); 2.37-2.42 (1H, br m, OH); 4.11-4.18 (4H, m, 2×CH$_2$).

IR ($v_{max}$, cm$^{-1}$, ATR): 3453brw, 2960m, 2930m, 1739s, 1462m, 1201s, 1094s, 996m.

MS [m/z (EI)]: 189 (M+H$^+$, <1%), 157 (M$^+$–CH$_2$OH, 2), 112 (13), 97 (3), 90 (12), 83 (27), 70 (74), 57 (100), 43 (59), 41 (51).

EXAMPLE 5

Hydroxy-acetic acid 2-butyl-octyl ester

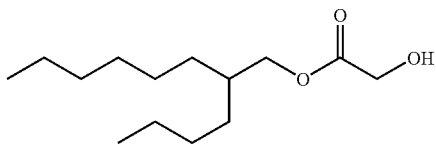

Hydroxy-acetic acid 2-butyl-octyl ester

H-NMR (400 MHz, CDCl$_3$, coupling constants in Hz): 0.83-0.93 (6H, m, 2×CH$_3$); 1.18-1.35 (16H, m, 8×CH$_2$); 1.62-1.70 (1H, m, CH); 2.40 (1H, t, J5, OH); 4.11 (2H, d, J6, CH$_2$); 4.15 (2H, d, J5, CH$_2$).

IR ($v_{max}$, cm$^{-1}$, ATR): 3459brw, 2926s, 2858m, 1740s, 1203s, 1096s, 933w.

MS [m/z (EI)]: 245 (M+H$^+$, <1%), 213 (M$^+$–CH$_2$OH, 11), 168 (12), 126 (14), 111 (44), 98 (25), 85 (32), 71 (47), 57 (100), 43 (77), 41 (51).

EXAMPLE 6

Hydroxy-acetic 2-hexyl-decyl ester

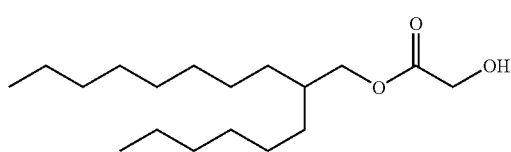

Hydroxy-acetic 2-hexyl-decyl ester

H-NMR (400 MHz, CDCl$_3$, coupling constants in Hz): 0.85-0.93 (6H, m, 2×CH$_3$); 1.18-1.35 (24H, m, 12×CH$_2$); 1.60-1.69 (1H, m, CH); 2.39-2.50 (1H, br, OH); 4.11 (2H, d, J6, CH$_2$); 4.15 (2H, s, CH$_2$).

IR ($v_{max}$, cm$^{-1}$, ATR): 3468brw, 2924s, 2855m, 1740m, 1204s, 1096s, 995w.

MS [m/z (EI)]: 301 (M+H$^+$, 9%), 269 (M$^+$–CH$_2$OH, 39), 224 (25), 154 (26), 139 (59), 111 (95), 97 (86), 83 (86), 71 (87), 57 (98), 43 (100), 41 (94).

EXAMPLES 7-9

The compounds of formula I-b with R$^1$=NH$_3^+$X$^-$ shown together with their spectroscopic data below are prepared as described in procedure B with the starting materials chosen as will be apparent to the skilled person.

EXAMPLE 7

2-Ethyl-hexyloxycarbonylmethyl-ammonium chloride

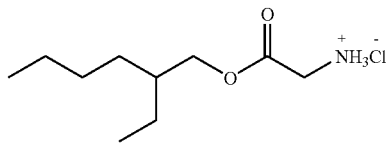

2-Ethyl-hexyloxycarbonylmethyl-ammonium chloride

H-NMR (400 MHz, CDCl$_3$, coupling constants in Hz): 0.80-0.93 (6H, m, 2×CH$_3$); 1.21-1.41 (8H, m, 4×CH$_2$); 1.53-1.63 (1H, m, CH); 3.95-4.05 (2H, m, CH$_2$); 4.06-4.14 (2H, m, CH$_2$); 9.49-9.71 (3H, br, NH$_3^+$).

IR ($v_{max}$, cm$^{-1}$, ATR): 2958m, 2929m, 1746s, 1222s, 1055m, 905m.

MS [m/z (EI)]: 188 (M–HCl+H$^+$, 15%), 157 (34), 149 (13), 112 (18), 36 (6), 30 (100).

EXAMPLE 8

2-Butyl-octyloxycarbonylmethyl-ammonium chloride

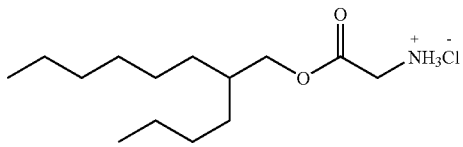

2-Butyl-octyloxycarbonylmethyl-ammonium chloride

H-NMR (400 MHz, CDCl$_3$, coupling constants in Hz): 0.82-0.95 (6H, m, 2×CH$_3$); 1.19-1.39 (16H, m, 8×CH$_2$); 1.55-1.68 (1H, m, CH); 3.99 (2H, d, J4, CH$_2$); 4.07 (2H, d, J8, CH$_2$); 8.54-8.69 (3H, br, NH$_3^+$).

IR ($v_{max}$, cm$^{-1}$, ATR): 2926s, 2857m, 1748s, 1228s, 1121m, 957m.

MS [m/z (EI)]: 244 (M–HCl+H$^+$, 2%), 213 (4), 168 (3), 76 (15), 57 (16), 43 (17), 36 (5), 30 (100).

EXAMPLE 9

2-Hexyl-decyloxycarbonylmethyl-ammonium chloride

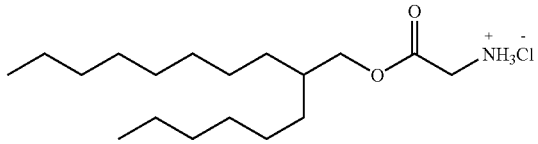

2-Hexyl-decyloxycarbonylmethyl-ammonium chloride

H-NMR (400 MHz, CDCl$_3$, coupling constants in Hz): 0.83-0.92 (6H, m, 2×CH$_3$); 1.19-1.35 (24H, m, 12×CH$_2$); 1.59-1.68 (1H, br, CH); 3.92-4.00 (2H, m, CH$_2$); 4.07 (2H, d, J6, CH$_2$); 8.59-8.73 (3H, br, NH$_3^+$).

IR ($v_{max}$, cm$^{-1}$, ATR): 2923s, 2854m, 1748m, 1226s, 1122m, 907w.

MS [m/z (EI)]: 300 (M–HCl+H$^+$, 2%), 269 (6), 111 (7), 76 (27), 57 (20), 43 (18), 36 (5), 30 (100).

EXAMPLE 10

Bacteriostatic Activity of the Compounds of the present Invention

The bacteriostatic effects of the compounds of the present invention are compared with those of known anti-bacterial agents against human skin bacteria. The results are shown below in Table 1.

The different axilla bacteria are isolated from the human axilla according to techniques known in the art, in particular according to standard microbiological practice. They are taxonomically identified by cell morphology, gram-reaction and biochemical tests included in the Api coryne test kit (BioMerieux, France). Strain *Staphylococcus epidermidis* Ax25 is identified by fatty acid methyl ester analysis (FAME; German type strain collection DSMZ, Germany). *Escherichia coli* DSM 682, *Staphylococcus aureus* DSM 799, and *Corynebacterium xerosis* DSM 20170 are obtained from the German-type strain collection.

The strains are maintained on Tryptic soy broth plates, this standard medium being supplemented with 5 g per litre of Polyoxyethylene Sorbitan Monooleate (Tween™ 80). Plates are incubated at 36° C. for a period 48 hours. The bacteria are then swabbed from the plates and suspended in 4 ml of Müller-Hinton broth supplemented with 100 mg of Tween™ 80 per litre (MH-Tween™) and incubated again at 36° C. for 16 hours. Following incubation, the bacterial suspensions are diluted in MH-Tween™ to obtain a final cell density of $10^7$ colony forming units per ml. These diluted suspensions of the different test organisms are distributed to different columns of a microtiter plate, 100 µl per well. The test compounds are dissolved in dimethylsulfoxide (DMSO) at various test concentrations and 2.5 µl of these different DMSO solutions are added to the different wells of the test plates. The plates are covered with plastic films and incubated for 24 h at 36° C. with shaking at 250 rpm. The turbidity developing in the microtiter plates is then examined after 24 h to determine microbial growth. The minimal concentration of test compounds inhibiting the growth of an organism by at least 80% is determined as the minimal inhibitory concentration (MIC).

Ax 25 was identified as *Staphylococcus epidermidis* by FAME analysis. Ax 7 is identified as *Corynebacterium* group G and Ax 15 as *Corynebacterium jeikeium* with the Api Coryne test kit. The latter two strains are isolated from the axilla of human volunteers and are able to generate axilla malodor when incubated in vitro with human axilla secretions.

From Table 1 it is apparent that, for all strains analysed, compounds of the present invention are better performing than the mono-ether (C2) and are comparable and better than the mono-ester (C1) and Farnesol (C3), which commonly are used in perfumes, personal care products and perfumed consumer goods. The compounds are particularly active against the odor forming skin bacteria and some of the compounds are more active then the chlorinated antibacterial compound Triclosan when tested against the malodor forming bacteria Ax7 and Ax15.

EXAMPLE 11

Bactericidal Activity of the Compounds of the Present Invention

The bactericidal effects of the compounds of the present invention are further tested. The results are shown below in Table 2. The bacteria are grown, harvested and diluted under the same conditions as described in example 10 above and added to microtiter plates (100 µl per well), each well con-

TABLE 1

Shows results for the MIC for human skin bacteria and standard bacterial reference strains of compounds of the invention and some comparative anti-bacterial agents. Data is expressed in % (weight/volume).

|    | S. epidermidis Ax 25 | C. xerosis DSM 20170 | Corynebacterium Ax 7 | Corynebacterium Ax 15 | Escherichia coli DSM 682 | Staphylococcus aureus DSM 799 |
|----|----------------------|----------------------|----------------------|-----------------------|--------------------------|-------------------------------|
| 1. | 0.125 | 0.125 | 0.125 | 0.125 | 0.125 | 0.25 |
| 2. | 0.008 | 0.008 | 0.008 | 0.004 | >0.25 | 0.031 |
| 3. | ≦0.0019 | >0.25 | 0.25 | 0.0039 | >0.25 | >0.25 |
| 4. | 0.063 | 0.031 | 0.031 | 0.031 | 0.063 | 0.063 |
| 5. | 0.002 | 0.002 | 0.001 | 0.001 | 0.002 | 0.008 |
| 6. | 0.0005 | 0.001 | 0.0005 | 0.0005 | 0.002 | 0.002 |
| C1 | <0.008 | 0.032 | 0.016 | 0.125 | >0.5 | 0.008 |
| C2 | 0.125 | 0.063 | 0.125 | 0.125 | 0.063 | 0.063 |
| C3 | 0.016 | 0.008 | 0.014 | 0.016 | >1 | 0.016 |
| C4 | 0.000015 | 0.0015 | 0.003 | 0.003 | 0.0005 | 0.0005 |

1. = Hydroxy-acetic acid 2-ethyl-hexyl ester

2. = Hydroxy-acetic acid 2-butyl-octyl ester

3. = Hydroxy-acetic 2-hexyl-decyl ester

4. = 2-Ethyl-hexyloxycarbonylmethyl-ammonium chloride

5. = 2-Butyl-octyloxycarbonylmethyl-ammonium chloride

6. = 2-Hexyl-decyloxycarbonylmethyl-ammonium chloride

C1 = Dodecanoic acid 2,3-dihydroxy-propyl ester: (1-mon-lauroyl-glycerol),

C2 = a commercial glycerol mono-ether: 3-(2-Ethyl-hexyloxy)-propane-1,2-diol,

C3 = Farnesol,

C4 = Triclosan taining 2.5 μl of the different DMSO solutions as described above. After 60 min incubation, 0.5 μl of the bacterial culture from each well (corresponding to $5 \times 10^3$ cfu in the control treatment) is transferred to a fresh microtiter plate which contained 100 μl per well of fresh medium. The plates are covered with plastic films and incubated for 24 h at 36° C. with shaking at 250 rpm. The turbidity developing in the microtiter plates is then examined after 24 h to determine microbial growth. The minimal concentration of test compounds which completely killed the bacterial inoculum is determined as the minimal bactericidal concentration (MBC).

TABLE 1

Shows results for the MIC for standard fungal strains. Data is expressed in % (weight/volume).

|    | C. albicans | A. niger |
|----|-------------|----------|
| 1. | 0.0625      | 0.125    |
| 5. | 0.0078      | 0.0039   |
| 6. | 0.0156      | 0.002    |

1. = Hydroxy-acetic acid 2-ethyl-hexyl ester
5. = 2-Butyl-octyloxycarbonylmethyl-ammonium chloride
6. = 2-Hexyl-decyloxycarbonylmethyl-ammonium chloride

TABLE 2

Shows the MBC for human skin bacteria and standard bacterial reference strains of compounds of the invention. Data is expressed in % (weight/volume).

|    | S. epidermidis Ax 25 | C. xerosis DSM 20170 | Corynebacterium Ax 7 | Corynebacterium Ax 15 | Escherichia coli DSM 682 | Staphylococcus aureus DSM 799 |
|----|----------------------|----------------------|----------------------|-----------------------|--------------------------|-------------------------------|
| 1. | 0.25                 | 0.125                | 0.125                | 0.125                 | n.d.                     | n.d.                          |
| 2. | >0.25                | >0.25                | >0.25                | >0.25                 | n.d.                     | n.d.                          |
| 3. | >0.25                | >0.25                | >0.25                | >0.25                 | >0.25                    | >0.25                         |
| 4. | 0.25                 | >0.25                | 0.25                 | 0.25                  | 0.125                    | 0.25                          |
| 5. | 0.004                | 0.004                | 0.002                | 0.002                 | 0.004                    | 0.004                         |
| 6. | 0.002                | 0.002                | 0.0005               | 0.0005                | 0.016                    | 0.004                         |

1. = Hydroxy-acetic acid 2-ethyl-hexyl ester
2. = Hydroxy-acetic acid 2- butyl-octyl ester
3. = Hydroxy-acetic 2-hexyl-decyl ester
4. = 2-Ethyl-hexyloxycarbonylmethyl-ammonium chloride
5. = 2-Butyl-octyloxycarbonylmethyl-ammonium chloride
6. = 2-Hexyl-decyloxycarbonylmethyl-ammonium chloride From Table 2 it is apparent that for all strains analysed, some compounds of the present invention have not only a bacteriostatic activity, but also the inherent potential to completely kill (i.e. bactericidal) an inoculum of $3 \times 10^3$ cfu within 60' contact time at a very low test concentration. The compounds are particularly active against the odor forming skin bacteria.

EXAMPLE 12

Antifungal Activity of the Compounds of the Present Invention

The fungistatic effects of the compounds of the present invention are tested against the standard strains *Candida albicans* and *Aspergillus niger*. The results are shown below in Table 3. The strains are maintained on Potato dextrose agar plates. Plates are incubated at 30° C. for a period of 72 hours. The fungal inoculum is then swabbed from the plates and suspended in Saboureaud liquid medium and incubated again at 30° C. for 24 hours in the case of *C. albicans*. For *A. niger* the inoculum containing the fungal spores is directly harvested from the agar plates and suspended in distilled water. The inoculum is then diluted in Saboureaud liquid medium to obtain a final cell density of $10^5$ colony forming units per ml. The test for fungistatic activity using differently concentrated DMSO stock solutions in microtiter plates is then conducted as described in example 10 for the bacteriostatic activity. The turbidity developing in the microtiter plates is then examined after 48 h to determine fungal growth. The minimal concentration of test compounds inhibiting the growth of an organism by at least 80% is determined as the minimal inhibitory concentration (MIC).

EXAMPLE 13

Aerosol Spray

|                                                      | I         | II        |
|------------------------------------------------------|-----------|-----------|
| Octyldodecanol                                       | 0.50      | 0.50      |
| Propylene Glycol                                     | 1.00      | 1.00      |
| Hydroxy-acetic acid 2-ethyl-hexyl ester              | 0.50      | —         |
| 2-Hexyl-decyloxycarbonylmethyl-ammonium chloride     | —         | 0.50      |
| Perfume                                              | q.s.      | q.s.      |
| Ethanol                                              | ad 100.00 | ad 100.00 |

The mixed liquid phase is filled with a mixture of propane-butane (2:7) in proportion of 39:61 in a spray can.

EXAMPLE 14

Roll-On Gel

|                                                      | I     | II    |
|------------------------------------------------------|-------|-------|
| Ethanol                                              | 50.00 | 50.00 |
| Polyoxyethylen-(20)-sorbitanmonolaurat               | 2.00  | 2.00  |
| Hydroxyethylcellulose                                | 0.50  | 0.50  |
| 2-Hexyl-decyloxycarbonylmethyl-ammonium chloride     | 0.50  | —     |
| Hydroxy-acetic acid 2-butyl-octyl ester              | —     | 0.30  |

-continued

|  | I | II |
|---|---|---|
| Aluminium Chlorohydrat | 10.00 | 10.00 |
| Perfume | q.s. | q.s. |
| Water | ad 100.00 | ad 100.00 |

EXAMPLE 15

Antiperspirant Stick

|  | I | II |
|---|---|---|
| Stearylalkohol | 25.00 | 20.00 |
| PEG-40 Hydrogenated Castor Oil | 2.00 | 3.00 |
| Cyclomethicone | ad 100 | ad 100 |
| Hydroxy-acetic acid 2-butyl-octyl ester | 0.50 | — |
| 2-Butyl-octyloxycarbonylmethyl-ammonium chloride | — | 0.50 |
| Aluminium Chlorohydrat, Powder | 20.00 | 25.00 |
| Perfume | q.s. | q.s. |

The invention claimed is:

1. A compound according to the formula I-a

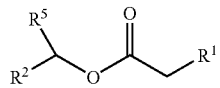

I-a wherein $R^1$ is selected from OH, $NH_2$ and $NH_3^+X^-$, wherein X is an inorganic anion, wherein $R^2$ is a singly-branched saturated or unsaturated aliphatic hydrocarbon moiety selected from $C_7$-$C_{15}$, wherein $R^5$ is selected from H, and a linear saturated or unsaturated aliphatic hydrocarbon moiety selected from $C_6$-$C_{14}$, and wherein $R^2$ and $R^5$ together have a total of 7 to 15 carbon atoms, and with the proviso that the ester compound is not selected from 2-ethylhexyl glycinate and ethylhexyl glycolate; optionally wherein $R^5$ is H and the compound is according to formula I-b

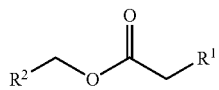

I-b wherein $R^1$ is selected from OH, $NH_2$ and $NH_3^+X^-$, wherein X is an inorganic anion, and wherein $R^2$ is a singly-branched saturated or unsaturated aliphatic hydrocarbon moiety selected from $C_7$-$C_{15}$.

2. The compound according to claim 1 wherein $R^2$ is saturated.

3. The compound according to claim 1 wherein $R^2$ is a hydrocarbon moiety according to formula II,

II wherein the bond between C1 and C2 (C1 and C2 being the carbon atoms in position 1 or 2 as indicated in formula II) is a single bond, or a double bond, and $R^3$ and $R^4$ are independently selected from methyl, ethyl, propyl, butyl, pentyl, hexyl, heptyl, octyl, nonyl, decyl, undecyl and dodecyl.

4. The compound according to claim 3 wherein the bond between C1 and C2 is a double bond.

5. The compound according to claim 4 selected from the group consisting of a compound with R3=ethyl and R4=propyl, a compound with R3=butyl and R4=methyl, a compound with R3=butyl and R4=pentyl, a compound with R3=hexyl and R4=propyl, a compound with R3=hexyl and R4=heptyl, and a compound with R3=octyl and R4=pentyl.

6. An anti-bacterial, anti-fungal or malodour-counteracting composition comprising a compound or mixture of compounds as defined in claim 1, optionally wherein the composition is selected from consumer products, household products, cosmetic and personal care products, products for use on the human body, products applied to the human skin, and perfumed consumer goods.

7. A composition according to claim 6 wherein the compound or mixture of compounds is present in an amount of from 0.1 to 5.0% by weight.

8. A composition according to claim 7 wherein the compound or mixture of compounds is present in an amount of from 0.1 to 1% by weight.

9. A composition according to claim 6 selected from consumer products, household products, cosmetic and personal care products, products for use on the human body, products applied to the human skin, and perfumed consumer goods.

10. Method of making an antibacterial, antifungal and/or a malodour-counteracting product by admixing an effective amount of an antibacterial, antifungal or malodour counteracting compound according to claim 1 to the product.

11. Method of making an antibacterial, antifungal and/or a malodour-counteracting product by admixing an effective amount of an antibacterial, antifungal or malodour counteracting compound to a product selected from cosmetic and personal care products, products for use on the human body, products applied to the human skin, and perfumed consumer goods; wherein the compound is according to the formula I-a

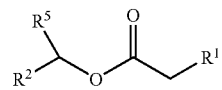

I-a wherein $R^1$ is selected from OH, $NH_2$, and $NH_3^+X^-$, wherein X is an inorganic anion, wherein $R^2$ is a singly-branched saturated or unsaturated aliphatic hydrocarbon moiety selected from $C_7$-$C_{15}$, wherein $R^5$ is selected from H, and a linear saturated or unsaturated aliphatic hydrocarbon moiety selected from $C_6$-$C_{14}$, and wherein R² and R⁵ together have a total of 7 to 15 carbon atoms; optionally wherein R⁵ is H and the compound is according to formula I-b

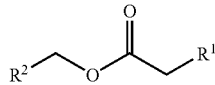

I-b wherein R¹ is selected from OH, NH₂ and NH₃⁺X⁻, wherein X is an inorganic anion, and wherein R² is a singly-branched saturated or unsaturated aliphatic hydrocarbon moiety selected from $C_7$-$C_{15}$.

12. The method according to claim 11 wherein R² is saturated.

13. The method according to claim 11 wherein R² is a hydrocarbon moiety according to formula II,

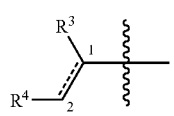

II wherein the bond between C1 and C2 (C1 and C2 being the carbon atoms in position 1 or 2 as indicated in formula II) is a single bond, or a double bond, and R³ and R⁴ are independently selected from methyl, ethyl, propyl, butyl, pentyl, hexyl, heptyl, octyl, nonyl, decyl, undecyl and dodecyl.

14. The method according to claim 13 wherein the bond between C1 and C2 is a double bond.

15. The method according to claim 14 wherein the compound is selected from the group consisting of a compound with R3=ethyl and R4=propyl, a compound with R3=butyl and R4=methyl, a compound with R3=butyl and R4=pentyl, a compound with R3=hexyl and R4=propyl, a compound with R3=hexyl and R4=heptyl, and a compound with R3=octyl and R4=pentyl.

16. An antibacterial, antifungal and/or a malodour-counteracting product prepared by the method of claim 11.

17. An antibacterial, antifungal and/or a malodour-counteracting product prepared by the method of claim 12.

18. An antibacterial, antifungal and/or a malodour-counteracting product prepared by the method of claim 13.

19. An antibacterial, antifungal and/or a malodour-counteracting product prepared by the method of claim 14.

20. An antibacterial, antifungal and/or a malodour-counteracting product prepared by the method of claim 15.

21. The compound according to claim 1 wherein R¹ is OH.

22. The compound according to claim 21 wherein R² is saturated.

23. The compound according to claim 21 wherein R² is a hydrocarbon moiety according to formula 11,

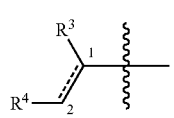

II wherein the bond between C1 and C2 (C1 and C2 being the carbon atoms in position 1 or 2 as indicated in formula II) is a single bond, or a double bond, and R³ and R⁴ are independently selected from methyl, ethyl, propyl, butyl, pentyl, hexyl, heptyl, octyl, nonyl, decyl, undecyl and dodecyl.

24. The compound according to claim 23 wherein the bond between C1 and C2 is a double bond.

25. The compound according to claim 24 selected from the group consisting of a compound with R3=ethyl and R4=propyl, a compound with R3=butyl and R4=methyl, a compound with R3=butyl and R4=pentyl, a compound with R3=hexyl and R4=propyl, a compound with R3=hexyl and R4=heptyl, and a compound with R3=octyl and R4=pentyl.

26. The compound according to claim 1 wherein R¹ is NH₂.

27. The compound according to claim 26 wherein R² is saturated.

28. The compound according to claim 26 wherein R² is a hydrocarbon moiety according to formula II,

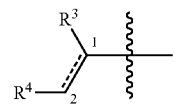

II wherein the bond between C1 and C2 (C1 and C2 being the carbon atoms in position 1 or 2 as indicated in formula II) is a single bond, or a double bond, and R³ and R⁴ are independently selected from methyl, ethyl, propyl, butyl, pentyl, hexyl, heptyl, octyl, nonyl, decyl, undecyl and dodecyl.

29. The compound according to claim 28 wherein the bond between C1 and C2 is a double bond.

30. The compound according to claim 29 selected from the group consisting of a compound with R3=ethyl and R4=propyl, a compound with R3=butyl and R4=methyl, a compound with R3=butyl and R4pentyl, a compound with R3=hexyl and R4=propyl, a compound with R3=hexyl and R4=heptyl, and a compound with R3=octyl and R4=pentyl.

31. The compound according to claim 1 wherein R¹ is NH₃⁺X⁻.

32. The compound according to claim 31 wherein R² is saturated.

33. The compound according to claim 31 wherein R² is a hydrocarbon moiety according to formula II,

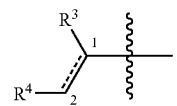

II wherein the bond between C1 and C2 (C1 and C2 being the carbon atoms in position 1 or 2 as indicated in fomula II) is a single bond, or a double bond, and R³ and R⁴ are independently selected from methyl, ethyl, propyl, butyl, pentyl, hexyl, heptyl, octyl, nonyl, decyl, undecyl and dodecyl.

34. The compound according to claim 33 wherein the bond between C1 and C2 is a double bond.

35. The compound according to claim 34 selected from the group consisting of a compound with R3=ethyl and R4=propyl, a compound with R3=butyl and R4=methyl, a compound with R3=butyl and R4=pentyl, a compound with R3=hexyl and R4=propyl, a compound with R3=hexyl and R4=heptyl, and a compound with R3=octyl and R4=pentyl.

36. The composition according to claim 6 wherein R¹ is OH.

37. The composition according to claim 36 wherein the compound or mixture of compounds is present in an amount of from 0.1 to 5.0% by weight.

38. The composition according to claim 6 wherein $R^1$ is $NH_2$.

39. The composition according to claim 38 wherein the compound or mixture of compounds is present in an amount of from 0.1 to 5.0% by weight.

40. The composition according to claim 6 wherein $R^1$ is $NH_3^+X^-$.

41. The composition according to claim 40 wherein the compound or mixture of compounds is present in an amount of from 0.1 to 5.0% by weight.

42. The method according to claim 11 wherein $R^1$ is OH.

43. The method according to claim 11 wherein $R^1$ is $NH_2$.

44. The method according to claim 11 wherein $R^1$ is $NH_3^+X^-$.

* * * * *